United States Patent [19]
Miller et al.

[11] Patent Number: 5,298,239
[45] Date of Patent: Mar. 29, 1994

[54] MUTATIONS RENDERING PLATELET GLYCOPROTEIN IB α LESS REACTIVE

[75] Inventors: Jonathan L. Miller; David Cunningham; Vicki A. Lyle, all of Syracuse; Clara N. Finch, Webster, all of N.Y.

[73] Assignee: The Research Foundation of State University of New York, Albany, N.Y.

[21] Appl. No.: 821,717

[22] Filed: Jan. 15, 1992

Related U.S. Application Data

[63] Continuation-in-part of Ser. No. 770,968, Oct. 7, 1991.

[51] Int. Cl.$^5$ .................. C12N 15/12; A61K 37/547; A61K 37/02
[52] U.S. Cl. ...................... 424/94.63; 424/94.64; 435/69.6; 435/172.3; 435/252.3; 435/320.1; 435/6; 530/381; 530/380; 530/395; 514/8; 536/23.5
[58] Field of Search .................. 530/380, 395, 381; 536/27, 23.5; 424/94.63, 94.64; 514/8; 435/69.1, 69.6

[56] References Cited

U.S. PATENT DOCUMENTS

| | | | |
|---|---|---|---|
| 4,683,291 | 7/1987 | Zimmerman et al. | 530/324 |
| 4,745,051 | 5/1988 | Smith et al. | 435/69.51 |
| 4,879,236 | 11/1989 | Smith et al. | 435/320.1 |

FOREIGN PATENT DOCUMENTS

| | | |
|---|---|---|
| 0279661 | 8/1988 | European Pat. Off. |
| 0317278 | 5/1989 | European Pat. Off. |
| 0370171 | 5/1990 | European Pat. Off. |
| WO89/00196 | 1/1989 | PCT Int'l Appl. |
| WO90/02566 | 3/1990 | PCT Int'l Appl. |

OTHER PUBLICATIONS

K. J. Clemetson et al., in *Molecular Biology and Differentiation of Megakaryocytes*, pp. 77-88 (Wiley-Liss, Inc. 1990).
A. Duperray et al., Abstract No. 26, Thrombosis and Haemostasis 65: 654 (Jun. 1991).
C. N. Finch et al., Blood 75: 2357-2362 (Jun. 1990).
R. I. Handin and E. Petersen, Abstract No. 477, Blood 74: 129A (Nov. 1989).
C. A. Hasemann and J. D. Capra, Proc. Natl. Acad. Sci. USA 87: 3942-3946 (May 1990).
J. A. Lopez et al., Proc. Natl. Acad. Sci. USA 84: 5615-5619 (Aug. 1987).
J. A. Lopez et al., Proc. Natl. Acad. Sci. USA 85: 2135-2139 (Apr. 1988).
J. A. Lopez et al., Abstract No. 2373, Circulation 82: III-597 (Oct. 1990).
V. A. Luckow and M. D. Summers, Bio/Technology 6: 47-55 (Jan. 1988).
S. Meyer et al., Abstract No. 350, Thrombosis and Haemostasis 65: 771 (Jun. 1991).
J. L. Miller, Clinics in Laboratory Medicine 4: 319-331 (Jun. 1984).
J. L. Miller et al., British Journal of Haemotology 74: 313-319 (1990).
J. L. Miller et al., Abstract No. 2364, Circulation 82: III-595 (Oct. 1990).
J. L. Miller et al., Proc. Natl. Acad. Sci. USA 88: 4761-4765 (Jun. 1991).
M. Murata et al., Abstract No. 1862, Blood 76: 468a (Nov. 1990).

(List continued on next page.)

*Primary Examiner*—Robert A. Wax
*Assistant Examiner*—Rebecca Prouty
*Attorney, Agent, or Firm*—Heslin & Rothenberg

[57] ABSTRACT

The subject invention provides purified polypeptide encoded by naturally-occurring wild-type platelet glycoprotein Ib alpha having a mutation which renders the polypeptide less reactive with von Willebrand factor. Preferably, the mutation is in the leucine rich region of GPIbα, such as the substitution of phenylalanine for leucine at residue 57. DNA encoding the mutant polypeptides, as well as expression systems for the production of the mutant polypeptides, are also provided. Methods and compositions using the mutant polypeptides and DNA oligomers complementary to the mutant polypeptides are further provided.

8 Claims, 6 Drawing Sheets

OTHER PUBLICATIONS

M. Murata et al., Abstract No. 348, Thrombosis and Haemostasis 65: 771 (Jun. 1991).

E. Petersen et al., Abstract No. 1251, Blood 72: 225a (Nov. 1988).

M. R. Pincus et al., Abstract No. 346, Thrombosis and Haemostasis 65: 770 (Jun. 1991).

G. J. Roth, Blood 77: 5-19 (Jan. 1991).

J. Ware et al., Proc. Natl. Acad. Sci. USA 87: 2026-2030 (Mar. 1990).

N. R. Webb and M. D. Summers, Technique-A Journal of Methods in Cell and Molecular Biology 2: 173-188 (Aug. 1990).

R. H. Wenger et al., Biochem Biophys Res Commun 156: 389-395. (Oct. 1988).

R. H. Wenger et al., Gene 85: 517-524 (1989).

A. N. Wicki et al., Abstract No. 828, Abstracts of the International Society of Thrombosis and Haemostasis Meeting, Brussels, Belgium (1987).

A. N. Wicki et al., Abstract No. 829, Abstracts of the International Society of Thrombosis and Haemostasis Meeting, Brussels, Belgium (1987).

A. N. Wicki et al., Thrombosis and Haemostasis 61: 448-453 (1989).

J. Wippler et al., Abstract No. 31, Thrombosis and Haemostasis 65: 655 (Jun. 1991).

J. Ware et al., Abstract No. 1101, Blood 78: 278a (Nov. 1991).

FIG. I

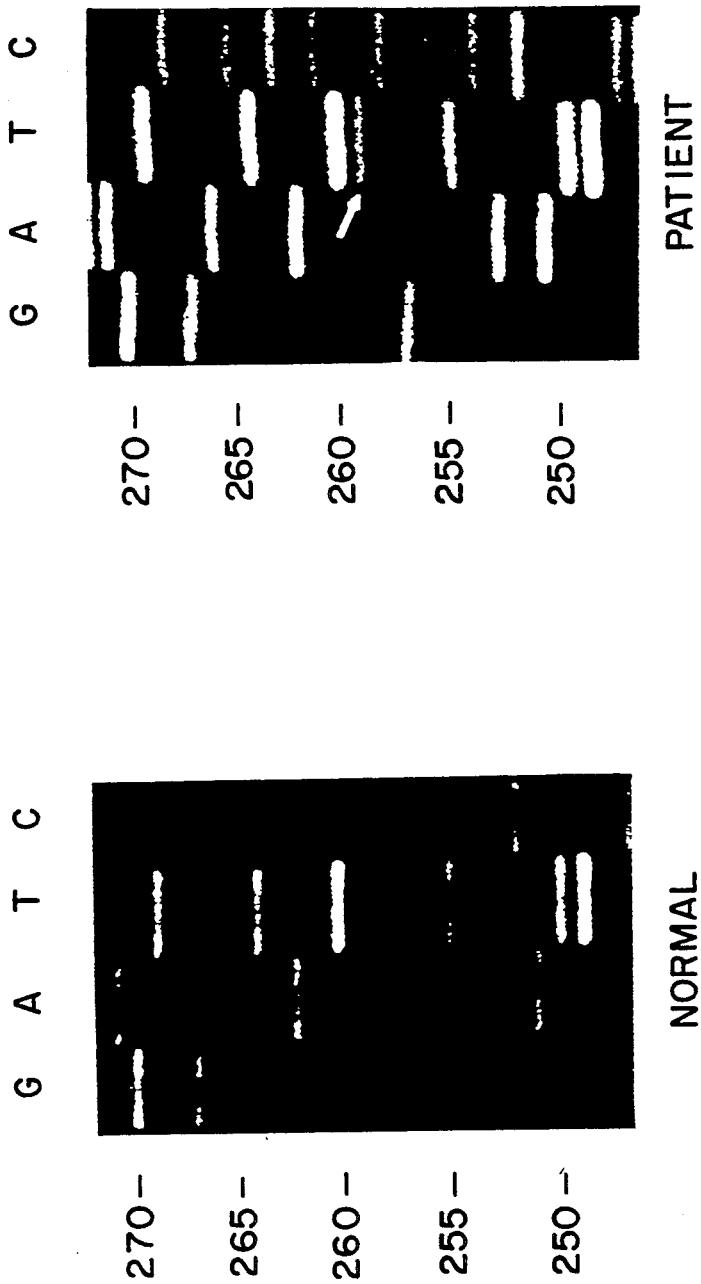

5,298,239

MUTATIONS RENDERING PLATELET GLYCOPROTEIN IB α LESS REACTIVE

This invention was made with support under National Heart, Lung, and Blood Institute Grant No. HL32853 of the National Institutes of Health. Accordingly, the U.S. Government has certain rights in the invention.

CROSS-REFERENCE TO RELATED APPLICATIONS

This application is a continuation-in-part of U.S. Ser. No. 770,968, filed Oct. 7, 1991, the contents of which are hereby incorporated by reference into the subject application.

TECHNICAL FIELD

This invention relates to the α chain of the platelet glycoprotein Ib (GPIbα). More particularly, the invention relates to mutations in the gene encoding GPIbα which render the glycoprotein less reactive with von Willebrand factor. Mutant polypeptides and their production and use are provided, with the preferred mutation being at residue Leu 57 of wild-type GPIbα.

BACKGROUND OF THE INVENTION

Throughout this application various publications are referenced by arabic numerals within parentheses. Full citations for these references may be found at the end of the specification immediately preceding the Sequence Listing. The disclosures of these publications in their entireties are hereby incorporated by reference in this application in order to more fully describe the state of the art to which the invention pertains.

The study of functional platelet disorders has traditionally consisted of a description of the abnormal responsiveness of patient platelets in a variety of experimental conditions, together with a genetic analysis of the families involved. In most cases, however, a precise correlate of abnormal functions with underlying abnormal structure has not been possible. Recently, the entire cDNA sequences encoding the protein chains comprising the platelet glycoprotein (GP) IIb/IIIa receptor (1-6) and the platelet GPIb/IX receptor (7-10) have been obtained, opening the possibility for study of the molecular basis of disorders affecting these receptors.

Bray and Shuman (11) first identified an abnormal gene coding for GPIIIa in one Glanzmann thrombasthenia family. A major deletion of genomic DNA coding for GPIIb (12) was subsequently described in another thrombasthenic patient. A nonsense mutation has also been reported in the GPIbα gene, leading to incomplete synthesis of the GPIbα protein in a patient with Bernard-Soulier disease (BSD) (13). A point mutation in the GPIbα gene coding for a valine in place of the wild-type glycine in the GPIbα of patients with platelet-type von Willebrand disease has also recently been identified and is disclosed in copending, coassigned U.S. Ser. No. 770,968, filed Oct. 7, 1991, of which the subject application is a continuation-in-part.

Absence of the GPIb/IX receptor for von Willebrand factor (vWF) is the hallmark of the autosomal recessive bleeding disorder, BSD. Applicants have previously described in preliminary form (15) a family in whom attributes of BSD appear to be transmitted in an autosomal dominant manner, and in whom there appears to be a qualitative, rather than quantitative, abnormality of GPIbα. Descriptions of apparently qualitative abnormalities of GPIbα have also been reported in patients of Italian (16) and Norwegian (17) origin.

The subject invention provides a molecular characterization of the abnormality in the American family applicants have studied.

SUMMARY OF THE INVENTION

The primary sequences of the three individual glycoprotein (GP) chains, GPIbα, GPIbβ, and GPIX, comprising the normal platelet GPIb/IX receptor for von Willebrand factor (vWF) have recently been determined, opening the possibility for characterization of disorders of this receptor at the molecular level. The presence of a leucine tandem repeat in each of these chains is of particular interest, because such repeats may be involved in associations between polypeptide segments.

Applicants disclose herein an autosomal dominant variant of Bernard-Soulier disease associated with a heterozygous substitution of phenylalanine for a highly conserved leucine residue within the GPIbα leucine tandem repeat. Affected individuals experienced a moderate bleeding tendency, thrombocytopenia, and an increased mean platelet volume. Platelet aggregation was decreased only in response to ristocetin or to asialo-vWF. The $K_d$ for $^{125}$I-vWF binding to patient platelets was significantly increased over control values at 0.5 mg/mL ristocetin, but was normal at 1.0 or 1.5 mg/mL ristocetin. While sodium dodecyl sulfate-polyacrylamide gel electrophoresis (SDS-PAGE) showed an essentially normal complement of all components of the GPIb/IX complex, a minor amount of a putative proteolytic fragment was identified that migrated faster than GPIb and was immunoreactive with polyclonal anti-GPIbα antibody, but not with a monoclonal antibody directed against the 45 Kd amino-terminal region of GPIbα. However, because the great majority of patient GPIbα comigrates with normal GPIbα, the major functional abnormalities of the patient platelets are most likely a consequence of the altered structure of the non-proteolyzed protein. Full concordance within the studied family between phenotypic expression and a heterozygous single nucleotide substitution in genomic DNA coding for a phenylalanine in place of the wild-type leucine at residue 57 of the mature GPIbα, absence of this substitution in 266 alleles from the normal population, and the lack of any other abnormality of patient DNA throughout the entire coding sequence for GPIbα provide strong support that this substitution constitutes a pathologic point mutation responsible for the observed phenotypic abnormalities. While the roles that leucine tandem repeats may normally play within the GPIb/IX complex are not yet known, the perturbation of such a repeat in GPIbα may impair interaction with other components of the complex and/or with the binding of vWF.

It is thus an object of the present invention to determine a structural abnormality within GPIbα itself which underlies a form of BSD. From studies at the genomic DNA and platelet RNA levels, the subject invention provides for a point mutation (phenylalanine for leucine 57) that results in an abnormality of the primary structure of platelet GPIbα in patients with a form of BSD. It is a further object of the subject invention to provide a recombinant polypeptide having this mutation and methods of producing and using the mutant polypeptide.

BRIEF DESCRIPTION OF THE FIGURES

These and other objects, advantages and features of the present invention will be more fully understood from the following detailed description of certain embodiments thereof when considered in conjunction with the accompanying drawings in which:

FIGS. 5A and 5B are a DNA sequence analysis of the GPIbα gene. Genomic DNA amplified by the primer pair J8/J14 (SEQUENCE ID NO:1 AND SEQUENCE ID NO:3, respectively) was cloned into M13mp18 and then sequenced. The heterozygous presence of a C and a T at nucleotide position 259 (arrow) in a pool of 70 individual M13mp18 clones of amplified DNA from patient III-2 (Patient) contrasts with the homozygous wild-type C seen in a normal individual (Normal)

DETAILED DESCRIPTION OF THE INVENTION

Figure 1:
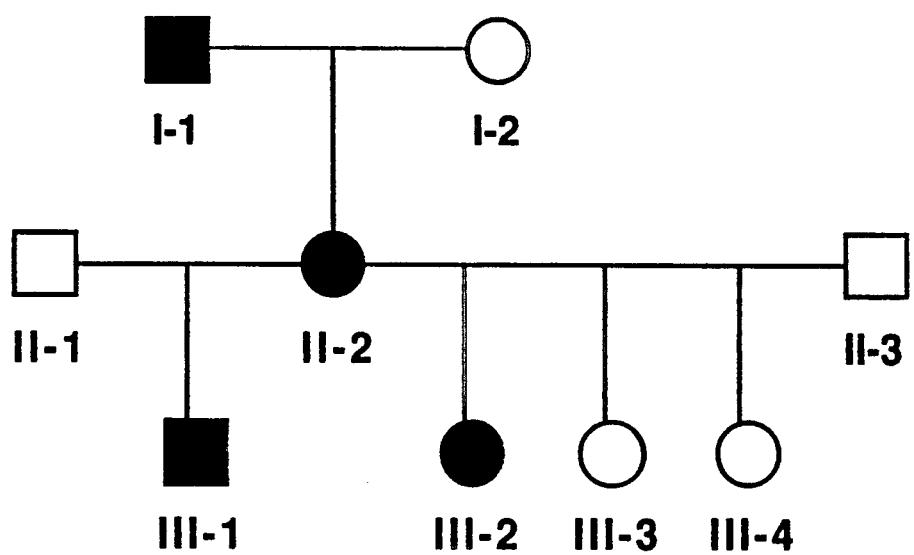
FIG. 1 is a family pedigree showing an autosomal dominant inheritance pattern. The proband (Patient III-1) and other relatives with a history of clinically significant bleeding are shown in solid symbols. Asymptomatic individuals are shown in open symbols.

The subject invention provides a purified polypeptide encoded by a DNA sequence, the DNA sequence comprising DNA encoding naturally-occurring wild-type platelet glycoprotein Ib alpha (GPIbα) having a mutation which renders the polypeptide encoded by the DNA less reactive with von Willebrand factor. All the references to map positions correspond to the identically numbered positions along the amino acid sequence of GPIbα shown on page 4 of European Patent Application Publication No. 0 317 278 A2, published May 24, 1989, and/or page 5617 of the Proc. Natl. Acad. Sci. USA article by J. A. Lopez et al., volume 84, pages 5615–5619. The European Application is entitled "Proteolytic fragments and synthetic peptides that block the binding of von Willebrand factor to the platelet membrane glycoprotein Ib" and was filed on behalf of Scripps Clinic and Research, with T. S. Zimmerman et al. listed as inventors. The sequence shown on page 4 of the European Application represents the sequence of the first 293 amino acids of naturally-occurring wild-type platelet glycoprotein Ib alpha. The article by Lopez et al. is entitled "Cloning of the α chain of human platelet glycoprotein Ib: A transmembrane protein with homology to leucine-rich $\alpha_2$-glycoprotein" and provides the amino acid sequence for the remainder of the GPIbα protein. The amino acid sequence of the naturally-occurring wild-type platelet glycoprotein Ib alpha is also given below:

SEQ ID NO: 6

| | | | | | | | | | | | | | | | |
|---|---|---|---|---|---|---|---|---|---|---|---|---|---|---|---|
| His | Pro | Ile | Cys | Glu | Val | Ser | Lys | Val | Ala | Ser | His | Leu | Glu | Val | Asn |
| | | | | | 5 | | | | | 10 | | | | | 15 |
| Cys | Asp | Lys | Arg | Asn | Leu | Thr | Ala | Leu | Pro | Pro | Asp | Leu | Pro | Lys | Asp |
| | | | | 20 | | | | | 25 | | | | | 30 | |
| Thr | Thr | Ile | Leu | His | Leu | Ser | Glu | Asn | Leu | Leu | Tyr | Thr | Phe | Ser | Leu |
| | | | 35 | | | | | 40 | | | | | 45 | | |
| Ala | Thr | Leu | Met | Pro | Tyr | Thr | Arg | Leu | Thr | Gln | Leu | Asn | Leu | Asp | Arg |
| | | 50 | | | | | 55 | | | | | 60 | | | |
| Cys | Glu | Leu | Thr | Lys | Leu | Gln | Val | Asp | Gly | Thr | Leu | Pro | Val | Leu | Gly |
| | 65 | | | | | 70 | | | | | 75 | | | | |
| Thr | Leu | Asp | Leu | Ser | His | Asn | Gln | Leu | Gln | Ser | Leu | Pro | Leu | Leu | Gly |
| 80 | | | | | 85 | | | | | 90 | | | | | 95 |
| Gln | Thr | Leu | Pro | Ala | Leu | Thr | Val | Leu | Asp | Val | Ser | Phe | Asn | Arg | Leu |
| | | | | 100 | | | | | 105 | | | | | 110 | |

-continued

| | | | | | | | | | | | | | | |
|---|---|---|---|---|---|---|---|---|---|---|---|---|---|---|
|Thr|Ser|Leu|Pro 115|Leu|Gly|Ala|Leu|Arg 120|Gly|Leu|Gly|Glu|Leu 125|Gln|Glu|

Leu Tyr Leu Lys Val Asn Glu Leu Lys Thr Leu Pro Pro Gly Leu Leu
       130             135          140

Thr Pro Thr Pro Lys Leu Glu Lys Leu Ser Leu Ala Asn Asn Asn Leu
145                  150          155

Thr Glu Leu Pro Val Gly Leu Leu Asn Gly Leu Glu Asn Leu Asp Thr
160            165          170          175

Leu Leu Leu Gln Glu Asn Ser Leu Tyr Thr Ile Pro Lys Gly Phe Phe
          180          185               190

Gly Ser His Leu Leu Pro Phe Ala Phe Leu His Gly Asn Pro Trp Leu
      195            200             205

Cys Asn Cys Glu Ile Leu Tyr Phe Arg Arg Trp Leu Gln Asp Asn Ala
210              215             220

Glu Asn Val Tyr Val Trp Lys Gln Gly Val Asp Val Lys Ala Met Thr
225              230          235          240

Ser Asn Val Ala Ser Val Gln Cys Asp Asn Ser Asp Lys Phe Pro Val
         245           250            255

Tyr Lys Tyr Pro Gly Lys Gly Cys Pro Thr Leu Gly Asp Glu Gly Asp
        260          265            270

Thr Asp Leu Tyr Asp Tyr Pro Glu Glu Asp Thr Glu Gly Asp Lys
      275          280          285

Val Arg Ala Thr Arg Thr Val Val Lys Phe Pro Thr Lys Ala His Thr
    290             295            300

Thr Pro Trp Gly Leu Phe Tyr Ser Trp Ser Thr Ala Ser Leu Asp Ser
305              310          315         320

Gln Met Pro Ser Ser Leu His Pro Thr Gln Glu Ser Thr Lys Glu Gln
         325           330          335

Thr Thr Phe Pro Pro Arg Trp Thr Pro Asn Phe Thr Leu His Met Glu
      340            345          350

Ser Ile Thr Phe Ser Lys Thr Pro Lys Ser Thr Thr Glu Pro Thr Pro
      355            360          365

Ser Pro Thr Thr Ser Glu Pro Val Pro Glu Pro Ala Pro Asn Met Thr
370              375          380

Thr Leu Glu Pro Thr Pro Ser Pro Thr Thr Pro Glu Pro Thr Ser Glu
385              390          395         400

Pro Ala Pro Ser Pro Thr Thr Pro Glu Pro Thr Pro Ile Pro Thr Ile
         405           410         415

Ala Thr Ser Pro Thr Ile Leu Val Ser Ala Thr Ser Leu Ile Thr Pro
        420          425          430

Lys Ser Thr Phe Leu Thr Thr Thr Lys Pro Val Ser Leu Leu Glu Ser
      435            440          445

Thr Lys Lys Thr Ile Pro Glu Leu Asp Gln Pro Pro Lys Leu Arg Gly
    450             455          460

Val Leu Gln Gly His Leu Glu Ser Ser Arg Asn Asp Pro Phe Leu His
465              470          475         480

Pro Asp Phe Cys Cys Leu Leu Pro Leu Gly Phe Tyr Val Leu Gly Leu
         485           490           495

Phe Trp Leu Leu Phe Ala Ser Val Val Leu Ile Leu Leu Leu Ser Trp
      500            505          510

Val Gly His Val Lys Pro Gln Ala Leu Asp Ser Gly Gln Gly Ala Ala
      515            520          525

Leu Thr Thr Ala Thr Gln Thr Thr His Leu Glu Leu Gln Arg Gly Arg
    530             535          540

-continued

| | | | | | | | | | | | | | | | |
|---|---|---|---|---|---|---|---|---|---|---|---|---|---|---|---|
| Gln | Val | Thr | Val | Pro | Arg | Ala | Trp | Leu | Leu | Phe | Leu | Arg | Gly | Ser | Leu |
| 545 | | | | | 550 | | | | | 555 | | | | | 560 |
| Pro | Thr | Phe | Arg | Ser | Ser | Leu | Phe | Leu | Trp | Val | Arg | Pro | Asn | Gly | Arg |
| | | | | 565 | | | | | 570 | | | | | 575 | |
| Val | Gly | Pro | Leu | Val | Ala | Gly | Arg | Arg | Pro | Ser | Ala | Leu | Ser | Gln | Gly |
| | | | 580 | | | | | 585 | | | | | 590 | | |
| Arg | Gly | Gln | Asp | Leu | Leu | Ser | Thr | Val | Ser | Ile | Arg | Tyr | Ser | Gly | His |
| | | 595 | | | | | 600 | | | | | 605 | | | |
| Ser | Leu | | | | | | | | | | | | | | |
| | 610 | | | | | | | | | | | | | | |

The polypeptides of the subject invention have a mutation in this naturally-occurring sequence which renders the mutant polypeptide less reactive with von Willebrand factor. This decreased reactivity, or hyporesponsiveness, can be demonstrated in the laboratory using ristocetin. Any other suitable means for determining the reactivity of the polypeptide with vWF can also be utilized to identify polypeptides which are "less" reactive with vWF, i.e. less reactive than naturally-occurring wild-type GPIbα.

In one embodiment of the subject invention, the mutation occurs within the leucine tandem repeat region of the DNA encoding the naturally-occurring wild-type platelet GPIbα. The leucine rich area is defined as the region including residue 36 to residue 200. Residues 200 to about 220 represent a flanking region to the leucine rich area. A similar flanking region of about 22 residues is found on the amino-terminal side of the leucine rich area. Residues 220 to 310 represent a "hinge" region, and residues 310 to 420 represent a serine/threonine rich area.

Applicants have determined that residues 36 to 200 of this leucine rich area are preferred sites for mutations that result in a mutant polypeptide having less reactivity with vWF. This is discussed in further detail below. Preferably, the mutation is at a leucine residue within the leucine rich region, such as residue 57 in the wild-type GPIbα. A substitution of phenylalanine for this leucine 57 is preferred, but other amino acids could also be substituted as also discussed in further detail below.

The polypeptides of the subject invention can be used as compositions (including pharmaceutical compositions) comprising an amount of the polypeptide effective to inhibit platelet adhesion/aggregation and a compatible carrier (pharmaceutically acceptable carrier for pharmaceutical compositions). For the purposes of this application, "platelet adhesion/aggregation" is a term which includes adhesion of platelets to a non-platelet surface; adhesion of platelets to other platelets; and aggregation of platelets to other platelets. Due to their decreased reactivity, the mutant polypeptides do not readily bind to vWF and therefore adhesion/aggregation of platelets containing the mutant polypeptides is inhibitied or reduced. Numerous other applications utilizing this inhibition of platelet adhesion/aggregation property would be readily apparent to those skilled in the art to which the subject invention pertains, such as in treatment or prevention of thrombosis or atherosclerosis.

One use of the subject invention is a method of reducing the aggregation of platelets by introducing a mutant platelet glycoprotein Ib alpha into the platelets, thereby rendering the platelets less reactive with von Willebrand factor. Because the platelets are less reactive with von Willebrand factor, aggregation of the platelets is reduced or inhibited.

Mutant platelet glycoprotein Ib alpha can be introduced into platelets by any suitable means known to those skilled in the art. For example, DNA encoding the mutant platelet glycoprotein Ib alpha can be transferred to cells involved in thrombopoesis (the series of developmental steps leading to the production of platelets) by known methods. Such methods include, for example, retrovirus-mediated gene transfer to megakaryocytes, megakaryocyte progenitor cells, or hematopoetic stem cells, or any other common method of gene transfer to cells involved in thrombopoesis.

Alternatively, mutant platelet glycoprotein Ib alpha can be introduced into platelets by transfer of mutant mRNA into the platelet. Suitable methods include, for example, lipofectin-mediated mRNA transfer or other means known to those skilled in the art.

Alternatively, platelets isolated from subjects having the mutation in their platelets can be used in the invention to reduce platelet aggregation by substituting the mutant platelets for some or all platelets of a subject having wild-type non-mutant polypeptides.

The polypeptides of the subject invention could also be labeled with a detectable marker, and used as imaging agents. The marker could be a radioactive isotope, an element opaque to X-rays, or a paramagnetic ion. Radioactive isotopes are commonly used in medicine and are well known to those skilled in the art. Representative examples include indium-111, technetium-99m, and iodine-123. Paramagnetic ions are also commonly used in medicine and include, for example, chelated metal ions of chromium (III), manganese (II), and iron (III). Imaging can be done through any of the methods known to those skilled in the art. These methods include but are not limited to X-ray, CAT scan, PET scan, NMRI, and fluoroscopy.

Similarly, the polypeptide can be bound to a thrombolytic agent, such as tissue plasminogen activator (TPA), urokinase, Streptokinase, prourokinase, Anisoylated Plasminogen-Streptokinase Activator Complex, TPA analogs, or a protease. The mutant polypeptides bound to a thrombolytic agent can be utilized to localize the thrombolytic agent to the site of a thrombus formation. As used in this application, "bound" encompasses polypeptides bound covalently, non-covalently, or conjugated. The polypeptides may be conjugated through other chemical moieties, including amino acid or polypeptide cross-linkers, which are standardly used in the art and are well known to those skilled in the art to which the invention pertains.

The subject invention provides nucleic acid molecules encoding the polypeptides of this invention, including cDNA and isolated genomic DNA. DNA encoding the mutant polypeptides of the subject invention can be isolated from patients with a form of BSD, as discussed below. DNA encoding the mutant polypeptides can also be obtained by subjecting wild-type GPIbα DNA to various procedures to generate the desired mutation therein. Such procedures are readily apparent to those skilled in the art, and include, for example, site-directed mutagenesis.

The mutant DNA can be utilized to express the mutant polypeptides in various host cells. Suitable host cells are any cells in which the DNA sequence encoding the mutant polypeptide has been introduced by recombinant DNA techniques, as long as the cell is capable of expressing the DNA sequence and producing the polypeptide product. The cell may be a bacterial cell, an insect cell, a yeast cell, a mammalian cell such as Chinese hamster ovary cells, or any other suitable cell. Suitable bacterial cells include *Escherichia coli* and *Pseudomonas aeruginosa*, as well as *Bacillus subtilis*. Suitable insect cells include SF9 or SF21 cells.

The host cells may contain the sequence encoding the mutant polypeptide in the body of a vector, such as a plasmid or a viral vector. The plasmid or viral vector is constructed by recombinant DNA techniques so that the sequence encoding the mutant polypeptide is incorporated at a suitable position in the molecule.

Specifically, a plasmid for expression of the polypeptide may comprise DNA encoding the polypeptide and DNA encoding suitable regulatory elements positioned relative to the DNA encoding the polypeptide so as to effect expression of the polypeptide in a suitable host cell. Plasmids and viral vectors can harbor a variety of suitable regulatory elements, including promoters and operators, ribosomal binding sites, and repressors.

A preferred viral vector for use with an insect host cell is the Baculovirus expression vector system. The Baculovirus expression vector system is described in detail in U.S. Pat. No. 4,745,051, issued May 17, 1988 (G. E. Smith and M. D. Summers, "Method For Producing A Recombinant Baculovirus Expression Vector") and U.S. Pat. No. 4,879,236, issued Nov. 7, 1989 (G. E. Smith and M. D. Summers, "Method For Producing A Recombinant Baculovirus Expression Vector"), the contents of each of which are hereby incorporated by reference into the subject application. "A Manual of Methods for Baculovirus Vectors and Insect Cell Culture Procedures" by M. D. Summers and G. E. Smith (1987, 1988 Texas Agricultural Station, College Station, Tex.) is also readily available to those skilled in the art and provides a practical laboratory description on how to utilize the Baculovirus expression vector system.

The subject invention thus also provides a baculovirus vector for expression of the mutant polypeptides which comprises the DNA encoding the polypeptide and DNA encoding suitable regulatory elements positioned relative to the DNA encoding the polypeptide so as to effect expression of the polypeptide in a suitable host cell. In the case of the baculovirus vector, the suitable host cell comprises an insect cell.

In general, the subject invention thereby provides a method of producing the mutant polypeptides which comprises expressing DNA encoding the polypeptide in a suitable host so that the polypeptide is produced, recovering the polypeptide so produced from the host, and purifying the polypeptide so recovered.

The invention also provides probes suitable for hybridizing to the DNA encoding the mutant polypeptide. Specifically, the invention provides a DNA oligomer comprising a DNA sequence complementary to DNA encoding naturally-occurring wild-type platelet glycoprotein Ib alpha having a mutation which renders the polypeptide encoded by the DNA less reactive with von Willebrand factor. As with the polypeptides of the subject invention, the DNA oligomer preferably comprises a complementary sequence which is complementary to the leucine rich region of the DNA encoding the naturally-occurring wild-type platelet glycoprotein Ib alpha (amino acids 36 to 200). A leucine residue such as amino acid 57 is the preferred site for mutations within the leucine rich region. At amino acid 57, the substitution of phenylalanine for the leucine present in the wild-type GPIbα is preferred, resulting in a DNA oligomer having the complementary sequence (SEQUENCE ID NO:5):

5' CTGAGTGAAGCGAGTG -3'

This represents the complement to the sense strand of the double-stranded mutant DNA sequence. It should be readily apparent to those skilled in the art that a sequence complementary to the anti-sense strand of the mutant DNA is also provided by the subject invention.

The DNA oligomer can be labeled with a detectable marker, such as a radiolabeled molecule, a fluorescent molecule, an enzyme, a ligand, or biotin. The labeled oligomer can then be utilized to detect a mutation in the DNA encoding naturally-occurring wild-type platelet glycoprotein Ib alpha so as to diagnose a form of Bernard-Soulier disease. This method comprises:

a) obtaining a blood sample from the subject;
b) treating the blood sample so as to expose DNA present in the blood sample;
c) contacting the exposed DNA with the labeled DNA oligomer under conditions permitting hybridization of the DNA oligomer to any DNA complementary to the DNA oligomer present in the blood sample, the DNA complementary to the DNA oligomer containing the mutation;
d) removing unhybridized, labeled DNA oligomer; and
e) detecting the presence of any hybrid of the labeled DNA oligomer and DNA complementary to the DNA oligomer present in the blood sample, thereby detecting the mutation and diagnosing a form of Bernard-Soulier disease.

MATERIALS AND METHODS

Subjects. Five patients from two generations of a Caucasian family from central New York State (patients II-2, III-1, III-2, III-3, and III-4) were available for study. The proband (patient III-1) was a 13-year-old male who was referred for evaluation of thrombocytopenia (80,000/μL) noted prior to dental extractions. The patient had had frequent episodes of epistaxis, one episode severe enough to result in hospitalization. Otherwise, he was in good health. The proband's mother (patient II-2) had a long history of increased bleeding, most notably menorrhagia severe enough to result in an eventual hysterectomy, epistaxis continuing into adulthood, profuse bleeding associated with tonsillectomy and most recently gastrointestinal tract bleeding of undefined origin. Of three daughters of patient II-2 by a second marriage, one (patient III-2) also had a history of menorrhagia and epistaxis. Patient III-3 was felt to have had exaggerated bleeding following tonsillectomy in early childhood, but was otherwise normal. Patient III-4 had an essentially negative bleeding history.

The father of the proband was not available for study, but has a negative bleeding history. The proband's maternal grandfather and grandmother were also unavailable for testing. The latter has a negative bleeding history, while the maternal grandfather has carried a history of easy bruising and excessive bleeding from minor trauma.

The normal population studied was comprised of 133 adults all of whom denied any history of increased bleeding. This population consisted of medical students and hospital personnel, representing a variety of ethnic backgrounds although primarily Caucasian. Informed consent for these studies was given by each subject, as approved by the Institutional Review Board for the Protection of Human Subjects at the SUNY Health Science Center at Syracuse.

Routine Hemostatic Studies

Bleeding times were obtained using the Simplate device (Organon Teknika, Durham, N.C.). Platelet count and mean platelet volume were determined with a Coulter Electronics (Hialeah, FL) S-Plus IV on EDTA-anticoagulated whole blood, with reference intervals based on the study of 120 normal adults.

Platelet Function Studies

Blood from normal volunteers or from patients was collected into 1/10 volume of 3.8% sodium citrate and the platelet-rich plasma (PRP) prepared by centrifugation at room temperature for 50-90 seconds at 900 g. Platelet aggregation and secretion studies were performed on this citrated PRP, using a Chronolog (Havertown, Pa.) lumi-aggregometer. For studies with asialo-vWF, native human vWF was purified from human cryoprecipitate (provided by the Greater Syracuse Chapter of the American National Red Cross) and digested with proteinase-free neuraminidase from *Vibrio cholera* (Calbiochem, LaJolla, Calif.), as previously described (18).

Platelet membrane glycoprotein analysis.

Blood from normal donors was collected in acid-citrate-dextrose (ACD), platelets washed multiple times in phosphate buffered saline (PBS) containing 2 mmol/L EDTA and $^3$H-labeled by the periodate-$^3$H-borohydride procedure (19). For immunoprecipitation studies, labeled platelets were solubilized with 0.5% (vol/vol) Nonidet P40 (NP-40) in the presence of the inhibitors iodoacetamide (10 mmol/L), phenylmethylsulfonylfluoride (1 mmol/L), and aprotinin (1%) (all obtained from Sigma Chemical Co., St. Louis, Mo.) and further processed as described by Miller et al. (20). Immunoprecipitates were subsequently prepared using $10^8$ platelet equivalents of NP-40 lysate incubated for 18 hours at 4° C. either with 7.5 μg of the anti-GPIb MoAb AS-7 (21) or with the anti-GPIX MoAb Beb-1 (22), together with 150 μL of goat anti-mouse immunoglobulin coupled to agarose beads (Sigma). The agarose beads were washed exhaustively in Tris-buffered saline with 0.1% NP-40, and the immunoprecipitate complexes were then eluted from the agarose beads in 5% sodium dodecyl sulfate (SDS) in 10 mmol/L Tris, pH 6.8, and electrophoresed either non-reduced or after reduction with 2% β-mercaptoethanol on 5% to 15% exponential gradient SDS-PAGE, using the discontinuous buffer method of Laemmli (23).

For Western blotting, gels were electrophoretically transferred to nitrocellulose by the method of Towbin et al. (24), put into 0.9% NaCl-10 mmol/L Tris-HCl, pH 7.4 (TBS) containing 5% fetal bovine serum (FBS) and 0.05% Tween 20 (Bio Rad, Richmond, Calif.) to saturate any free binding sites, and then incubated with polyclonal rabbit antibody raised against the purified alpha chain of human platelet GPIb for 1.5 hours at 22° C. After three washes in TBS-Tween, the blots were then incubated with a 1:750 dilution of peroxidase-conjugated F(ab')$_2$ goat anti-rabbit IgG (Cooper Biomedical, Malvern, Pa.) in TBS-Tween-FBS for an additional 1.5 hours, then washed again three times in TBS-Tween, and finally incubated at 22° C. in TBS containing 0.5 mg/mL 4-chloro-1-naphthol (Sigma) and 0.015% $H_2O_2$ (wt/vol) for color development.

Radioligand binding studies

Platelets from normal or patient blood anticoagulated with ACD were washed by the albumin density gradient method of Walsh et al. (25) and resuspended to 50,000 platelets/μL in modified Tyrode's buffer containing 2% bovine serum albumin (BSA), pH 7.3. To 90 μL of this platelet suspension was added 25 μL of Tyrode-BSA buffer, pH 7.3, and 25 μL of serial dilutions (20 to 0.625 μg/mL) of $^{125}$I-vWF labeled by the method of Fraker and Speck (26). Ristocetin was then added (15 μL) at 0.5, 1.0, or 1.5 mg/mL, and after 1 hour of incubation at room temperature under non-stirring conditions, 50 μL of the platelet suspension was centrifuged through 300 μL of 20% sucrose in modified Tyrode-BSA buffer (27) and the platelet-associated radioactivity counted. Scatchard analysis of binding data was performed with the LIGAND (Scafit) computer program (28), Fortran version 2.3.10 for the IBM PC.

Preparation of DNA and RNA for Analyses

The preparation of genomic DNA from peripheral blood leukocytes and cDNA from platelet RNA were as previously described (14). DNA was amplified by the polymerase chain reaction (PCR) using primer pairs based on the published genomic DNA sequence of GPIbα (7). Primers J5a, J8 and J14 (SEQUENCE ID NO:2, SEQUENCE ID NO:1 and SEQUENCE ID NO:3, respectively) have been described elsewhere (14) and correspond to nucleotide positions 728–758, 38–60, and 1964–1987, respectively. For DNA sequence analysis the full-length coding region for mature GPIbα was amplified with primers J8 (SEQUENCE ID NO:1) and J14 (SEQUENCE ID NO:3). Each 100 μL reaction was in buffer consisting of 10 mmol/L Tris-HCl pH 8.3, 0.5 mmol/L MgCl$_2$, 50 mmol/L KCl, 10 pmoles of each dNTP, 50 pmoles of each primer, 5 U Ampli Taq DNA Polymerase (Perkin Elmer Cetus, Norwalk, Conn.), and 1 μg of genomic DNA. Thermocycling was in an Eppendorf MicroCycler (Eppendorf Inc., Fremont, Calif.) for 35 cycles of 20 seconds at 96° C., 1 minute at 55° C., and 4 minutes at 75° C. Products from four individual PCR reactions were pooled, purified by agarose gel electrophoresis, and cloned into M13mp18 and M13mp19. Single-stranded DNA templates were then prepared from pools of 70 clones in each vector.

For allele-specific hybridizations, the GPIbα coding region between bases 60 and 728 was amplified from either genomic DNA or cDNA with primers J8 (SEQUENCE ID NO:1) and J5a (SEQUENCE ID NO:2). PCR reactions were as above except that MgCl$_2$ was at 2 mmol/L and each reaction contained 1 U Taq polymerase and 50 pmole each of J8 (SEQUENCE ID NO:1) and J5a (SEQUENCE ID NO:2). Thermocycling was for 40 cycles of 1 minute at 94° C., 2 minutes at 56° C., and 2 minutes at 72° C.

DNA sequence Analysis

Dideoxy sequence analysis was performed by standard methods (29) using Sequenase (US Biochemicals, Cleveland, Ohio), $\alpha\text{-}^{35}\text{S-dATP}$ (Amerscham Corp., Arlington Heights, Ill.), and the appropriate primers.

Allele-specific Hybridizations

Sequences for allele-specific oligonucleotides (16-mers) were determined by applicants, and prepared for applicants by Genosys (The Woodlands, Tex.) using standard DNA synthesis technology. J18 (SEQUENCE ID NO:4) is an anti-sense oligonucleotide probe (5'-CTGAGTGAGGCGAGTG-3') that is the complement of the published GPIbα sequence from nucleotides 252 to 267. J19 (5'-CTGAGTGAAGCGAGTG-3') (SEQUENCE ID NO:5) differs from J18 (SEQUENCE ID NO:4) only at the position corresponding to nucleotide 259, where an A (complement of T) is present instead of a G (complement of the wild-type C), reflecting the single base difference observed in the GPIbα coding sequence of patient DNA. Probes were end-labeled using $\alpha\text{-}^{32}\text{P-ATP}$ and T4 polynucleotide kinase (29), and had a specific activity of 3 μCi/pmole. Amplified DNA was denatured in 0.4N NaOH, 25 mmol/L EDTA. Approximately 25 ng of each sample was then applied to each duplicate Gene Screen Plus (Dupont New England Nuclear, Boston, Mass.) nylon membrane using a Bio-Dot spotting apparatus (Bio Rad). The DNA was fixed to the nylon by ultraviolet irradiation of damp membranes for 5 minutes (Model TM-20 Transilluminator, UV Products, San Gabriel, Calif.). Membranes were then prehybridized for 1 hour at 65° C. each in 10 mL 6×SSC, 0.5% SDS, 10 mmol/L sodium phosphate, pH 6.8, 1 mmol/L EDTA containing 120 μg/mL denatured salmon sperm DNA. Labeled probe (either J18 [SEQUENCE ID NO:4] or J19 [SEQUENCE ID NO:5]) was then added at 0.5 pmol/mL, and membranes were hybridized for 2 hours at 49° C. (for J18 [SEQUENCE ID NO:4]) or 46° C. (for J19 [SEQUENCE ID NO:5]). Membranes were then washed once for 5 minutes at room temperature in 2×SSC, 0.1% SDS, followed by a high stringency wash in 6×SSC, 0.1% SDS for 5 minutes at 49° C. (for J18 [SEQUENCE ID NO:4]) or 46° C. (for J19 [SEQUENCE ID NO:5]). Autoradiography was then performed on the air-dried membranes.

RESULTS

The history of phenotypic expression in this kindred (FIG. 1), and in particular the involvement of both the proband (patient III-1) and a half-sister (patient III-2)—who are the offspring of a symptomatic mother (patient II-2) but of two unrelated (and asymptomatic) fathers—provides strong evidence that the bleeding disorder in this family follows a pattern of autosomal dominant transmission. The results of routine hemostatic studies are shown in Table 1. Affected individuals experienced a moderate bleeding tendency, which appeared to vary in severity over the course of multiple clinic visits. However, they consistently exhibited thrombocytopenia and an increased mean platelet volume. Platelet aggregation responses to ADP, collagen, and γ-thrombin (gamma thrombin) were normal in all patients studied.

TABLE 1

| | Family Studies | | | | |
|---|---|---|---|---|---|
| | II-2 | III-1 | III-2 | III-3 | III-4 |
| Bleeding Episodes | Tooth Extractions Tonsillectomy Menorrhagia | Severe Epistaxis Tooth Extractions | Epistaxis Menorrhagia | Negative History | Negative History |
| Bleeding Time (2–8 min) | 5 | 8.5–23 | 5.5–14.5 | 8 | 4 |
| Platelet Count (150–400 × 10³/L) | 65–81 | 63–128 | 87–109 | 306 | 403 |
| Platelet Volume (6.9–10.4 fL) | 18.3–21.2 | 19.9–21.1 | 14.5–15.9 | 8.9 | 7.1 |
| PRP Platelet Aggregation | | | | | |
| Ristocetin (1.2 mg/mL) | Decreased | Decreased | Decreased | Normal | Normal |
| Ristocetin (1.2 mg/mL) + 2 U/mL vWF | Not Performed | Decreased | Decreased | Not Performed | Not Performed |
| Collagen (20 μg/mL) | Normal | Normal | Normal | Normal | Normal |
| ADP (8 μmol/L) | Normal | Normal | Not Performed | Normal | Not Performed |
| Gamma Thrombin (135 nmol/L) | Normal | Normal | Normal | Normal | Normal |

Figure 2:
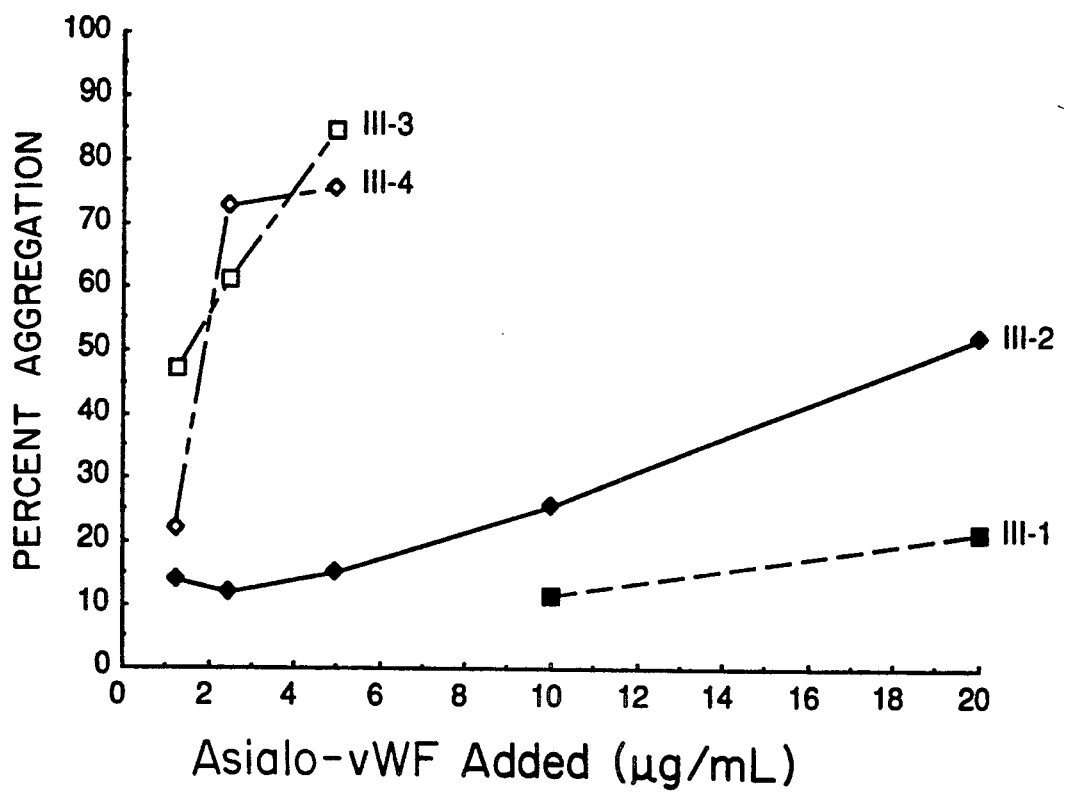
FIG. 2 shows asialo-vWF-induced aggregation of platelets. Platelet-rich plasma (PRP) was maintained at 37° C. and stirred at 1200 rpm. Asialo-vWF was added at the indicated final concentrations. Percent aggregation (i.e., maximal extent of aggregation) of patients III-3 and III-4 is indistinguishable from that of normal controls, whereas that of patients III-1 and III-2 is decreased.

In contrast, ristocetin-induced aggregation was characteristically decreased. However, even with respect to a single patient, the degree of this decrease was quite variable over time. Thus, at the time of his initial study the proband's platelets exhibited 6% aggregation in response to 1.2 mg/mL ristocetin, yet in an identical study 2 years later, showed 43% aggregation. In each case, the addition of exogenous vWF did not significantly affect this response. The platelets from patients II-2 and III-2 showed 28% to 48% aggregation in response to 1.2 mg/mL ristocetin, whereas those from the clinically unaffected siblings, patients III-3 and III-4, showed much stronger responses (91% to 100%). The platelets from patients III-1 and III-2 additionally showed a decreased responsiveness to aggregation by asialo-vWF (FIG. 2). In contrast, platelets from patients III-3 and III-4 produced full aggregation in response to concentrations of asialo-vWF (2 to 10 μg/mL) that produce identical results in normal individuals (18).

To study possible quantitative abnormalities of the vWF receptor, we performed binding studies of native vWF to patient and normal platelets. In the presence of ristocetin, $^{125}$I-vWF showed saturable binding kinetics over the range of 0.5 to 1.5 mg/mL ristocetin both in normals and in patients. At 1.0 and 1.5 mg/mL ristocetin, the apparent $K_d$ of $^{125}$I-vWF binding to patient platelets was indistinguishable from that to normal platelets (Table 2). In contrast, at 0.5 mg/mL ristocetin, a significantly (P<0.001) higher apparent $K_d$ was observed with patient platelets. Although total vWF bound to normal platelets typically exceeded that bound to patient platelets, such a difference was not statistically significant at any of the three ristocetin concentrations studied.

TABLE 2

| | $^{125}$I-vWF Binding to Washed Platelets | | | | |
|---|---|---|---|---|---|
| Ristocetin | Patient III-1 | Patient III-2 | Patient Mean | Control Group | P Value |
| 0.5 mg/mL | | | | | |
| $K_d$* | 3.70 | 4.34 | 4.02 | 1.39 ± 0.29 | <0.001 |
| $B_{Max}$ | 1.24 | 2.03 | 1.64 | 1.95 ± 0.60 | 0.535 |
| 1.0 mg/mL | | | | | |
| $K_d$ | 1.00 | 0.73 | 0.87 | 0.91 ± 0.22 | 0.798 |
| $B_{Max}$ | 1.38 | 1.41 | 1.40 | 2.25 ± 0.83 | 0.213 |
| 1.5 mg/mL | | | | | |
| $K_d$ | 0.83 | 0.74 | 0.79 | 0.75 ± 0.18 | 0.773 |
| $B_{Max}$ | 1.36 | 1.61 | 1.48 | 2.44 ± 1.01 | 0.253 |

Platelets from freshly drawn blood were washed by albumin density gradient centrifugation, suspended in modified Tyrode medium, and incubated with varying dilutions of $^{125}$I-vWF and ristocetin, as described in Materials and Methods. The platelets were then centrifuged through a layer of 20% sucrose containing 2% BSA, and the platelet-associated radioactivity counted. Data represent the specific binding of vWF, based on estimates of 0.3% to 2.6% nonspecific binding by the LIGAND (28) non-linear curve fitting program. Control group data are mean ± SD, n = 6. Statistical significance for difference of patient mean from control mean was analyzed by the unpaired, two-tailed t-test; a significant probability (P Value) was achieved only for the $K_d$ at a ristocetin concentration of 0.5 mg/mL.

*$K_d$, apparent dissociation constant in μg/mL.

$B_{Max}$, maximal binding in μg/10$^8$ platelets.

Figure 3B:
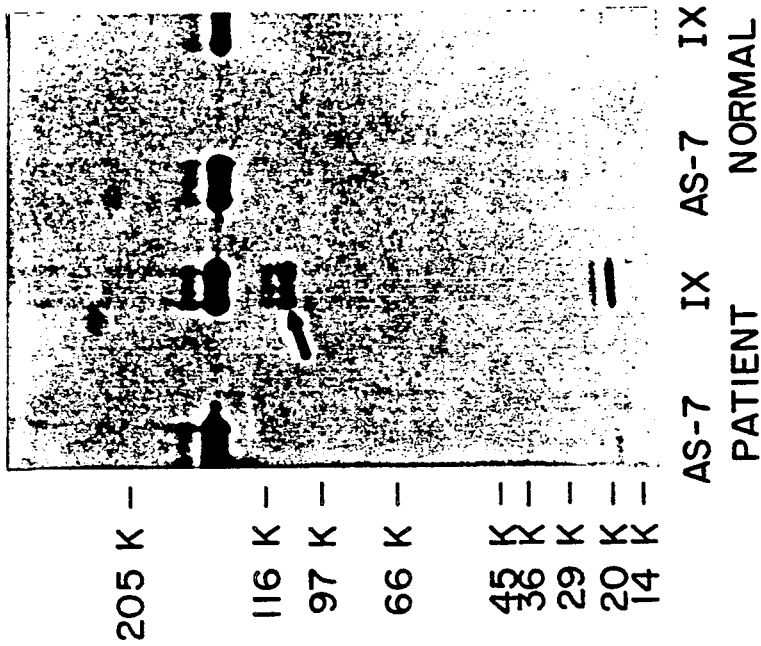
FIGS. 3A and 3B are an autoradiograms of SDS-PAGE (5% to 15% exponential gradient) showing immunoprecipitates with a monoclonal antibody (MoAb) directed against GPIb (AS-7) or a MoAb directed against GPIX (IX) obtained with $^{125}$I-labeled platelets from patient II-2 (PATIENT) or from a normal (NORMAL) control. The arrows point to bands (140 Kd non-reduced, 115 Kd and 105 Kd reduced) observed only in the anti-GPIX immunoprecipitates of the patient.
Figure 3A:
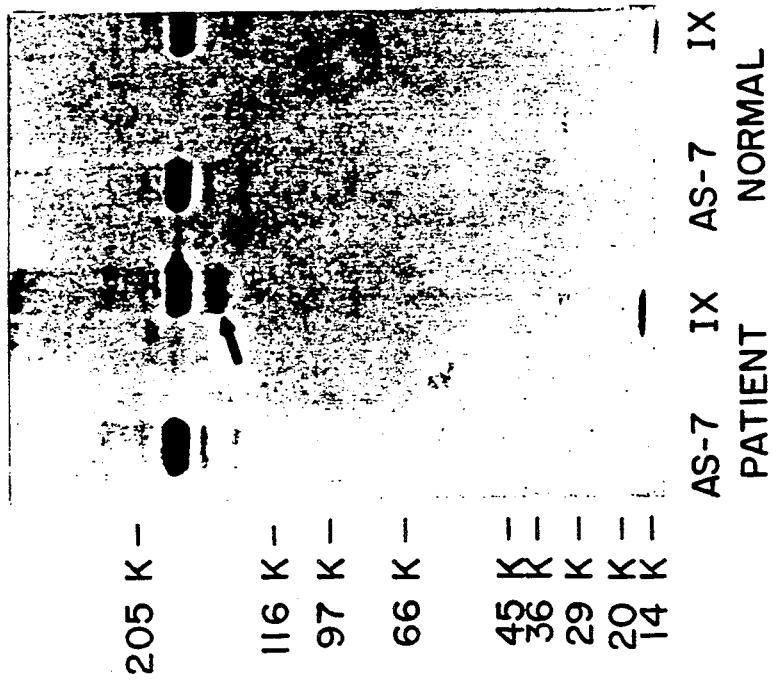
Figure 4:
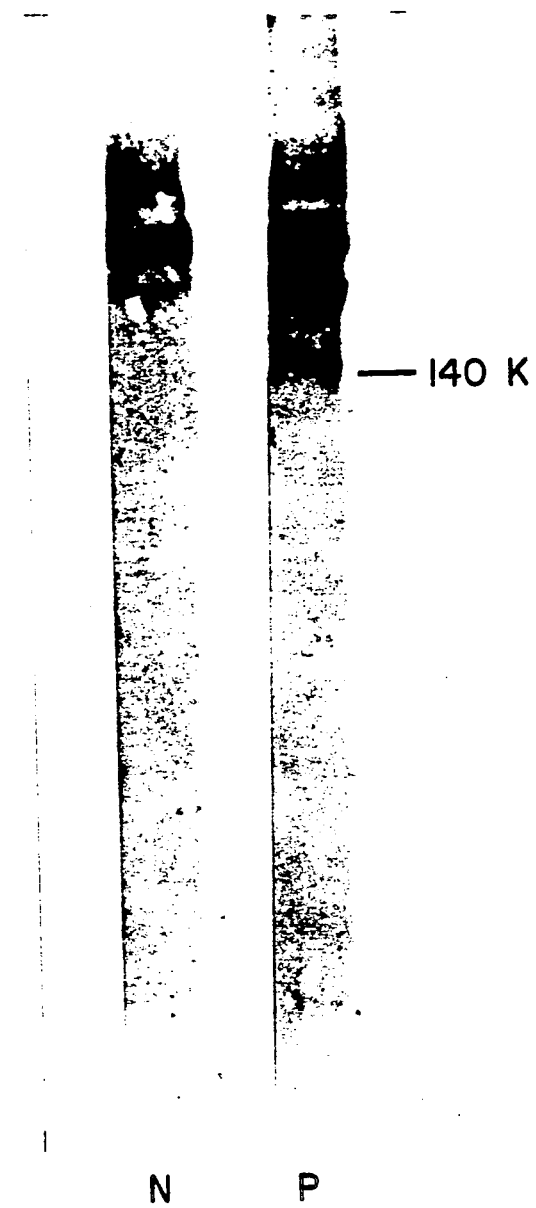
FIG. 4 is a western blot of normal (N) and patient (P) immunoprecipitates of platelet lysates run on 5% to 15% SDS-PAGE (non-reduced), electrophoretically transferred to nitrocellulose, and immunoblotted with polyclonal rabbit antibody directed against the alpha chain of human platelet GPIb. The line indicates a band of 140 Kd, identified in the patient sample only, that migrates at a faster rate than the GPIb seen above this band in both the patient and normal samples.

Platelets from the affected patients showed an essentially normal complement of the components of the GPIb/IX complex, as detected by SDS-PAGE of immunoprecipitates with AS-7, a MoAb recognizing an epitope in the amino-terminal region of GPIbα (21) (FIG. 3), or of whole detergent lysates (data not shown). While not seen in AS-7 immunoprecipitates, an additional band of 140 Kd non-reduced (bands of 115 Kd and 105 Kd reduced) coprecipitated with an antibody directed against GPIX in patient lysates (FIG. 3, arrows). These new bands consistently represented a relatively small proportion of the total glycoprotein precipitable by the anti-GPIX MoAb, as determined by scanning densitometry of the gels. For example, the 140 Kd band (non-reduced) seen in the experiment shown in FIG. 3 represented only 23% as much density as the patient band comigrating with normal GPIb, and the 115 Kd and 105 Kd bands (reduced) showed only 4% and 13%, respectively, as much density as the patient band comigrating with normal GPIbα. When platelet lysates immunoprecipitated with the anti-GPIX MoAb were electrophoresed and subsequently transferred to nitrocellulose, Western blotting with a polyclonal anti-GPIbα antibody confirmed that the 140 Kd (non-reduced) patient band was indeed a derivative of the GPIbα chain (FIG. 4). The polyclonal anti-GPIbα antibody also stained a band migrating immediately below that of intact GPIb. While the intensity of staining of this band was greater in the patient than in the normal control, this immunoreactive derivative of GPIbα, unlike the 140 Kd band, was not unique to patient platelets and likely reflects normal proteolytic degradation of GPIb, although possibly at a heightened rate.

Because the entire protein coding region of the GPIbα gene is contained within a single exon (30,31), we were able to perform DNA sequence analysis using genomic DNA obtained from circulating leukocytes. Using a series of oligonucleotide PCR primer pairs (14), we consistently observed identically migrating bands of amplified DNA in patients as compared with normal controls, suggesting the absence of any major deletions within the gene. DNA sequencing of patient III-2 confirmed the absence of any substitutions or deletions of nucleotides, as compared with the normal genome, throughout the entire protein coding region, with a single exception. At nucleotide 259 the patient DNA showed a heterozygous substitution of a T for the C normally present at this position (FIG. 5). This substitution was nonconservative, resulting in the replacement of a phenylalanine for a leucine at residue 57 of the mature GPIbα molecule.

Figure 6A:
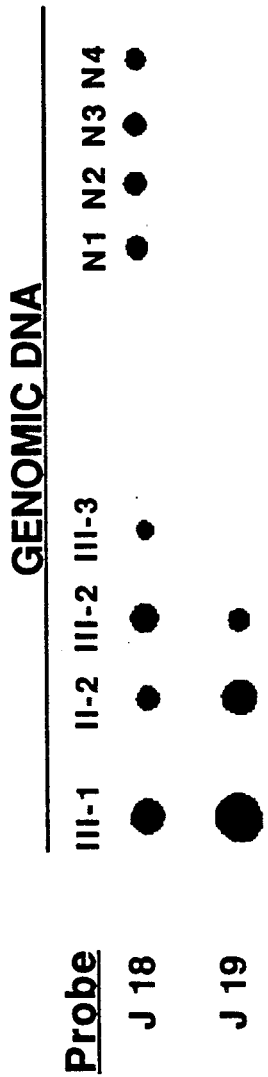
FIGS. 6A and 6B show an allele-specific oligonucleotide hybridization for the C to T mutation at nucleotide 259 of GPIbα. (A) Genomic DNA of patients II-2, III-1, III-2, and III-3, or of normal controls (N1 through N4), was hybridized, as described in Materials and Methods, both with the wild-type probe J18 (SEQUENCE ID NO:4) and with probe J19 (SEQUENCE ID NO:5) that detects the substitution of a T for the wild-type C at nucleotide position 259. (B) DNA obtained by PCR of reverse-transcribed platelet RNA from patient III-2 or from a normal control (N) was hybridized with probes J18 (SEQUENCE ID NO:4) and J19 (SEQUENCE ID NO:5), as described in Materials and Methods.

The single base substitution at nucleotide 259 did not create or destroy the recognition sequence of any known restriction enzyme. Allele-specific hybridization was used to determine the distribution of this substitution in family members and in the normal population. As shown in FIG. 6A, probe J19 (SEQUENCE ID NO:5), which detects the substituted T at position 259, hybridized with genomic DNA from all affected patients studied, but not from normal controls or from the phenotypically normal patient III-3; probe J19 (SEQUENCE ID NO:5) similarly did not hybridize with genomic DNA from patient III-4 (data not shown). In contrast, probe J18 (SEQUENCE ID NO:4), which detects the wild-type C at position 259, hybridized to the genomic DNA from all affected patients, from the unaffected family members (patients III-3 and III-4), and from the normal controls. This technique accordingly confirmed that the substitution was heterozygous in the affected family members. Allele-specific hybridization with probes J18 (SEQUENCE ID NO:4) and J19 (SEQUENCE ID NO:5) was studied with the genomic DNA from 133 normal individuals. In all cases only probe J18 (SEQUENCE ID NO:4) showed hybridization, indicating a wild-type pattern for all 266 alleles.

Figure 6B:
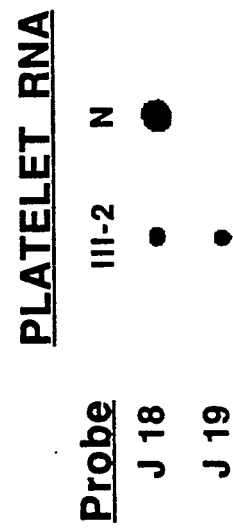

Expression of this substitution in patient platelets was investigated by PCR analysis of reverse-transcribed platelet messenger RNA (mRNA). As in the case of genomic DNA, no gross deletions were seen in patient samples. Allele-specific hybridization of cDNA reverse-transcribed from the platelet mRNA of patient III-2 identified expression of both the wild-type and substituted sequences, whereas only the wild-type sequence was identified in normals (FIG. 6B).

DISCUSSION

This study provides the first demonstration of a specific amino acid substitution in a component of the platelet GPIb/IX receptor complex for vWF in patients exhibiting a BSD phenotype. Full concordance within the studied family between phenotypic expression and a heterozygous single nucleotide substitution in genomic DNA coding for a phenylalanine in place of the wild-type leucine at residue 57 of the mature GPIbα, absence of this substitution in 266 alleles from the normal population, and the lack of any other abnormality of patient DNA throughout the entire coding sequence for GPIbα, provide strong support that this substitution constitutes a pathologic point mutation responsible for the observed phenotypic abnormalities.

Glycoprotein analyses of patient platelets showed the presence of a 140 Kd band (non-reduced) that migrates faster than normal GPIb on SDS-PAGE gels, but that shows immunologic reactivity with polyclonal anti-GPIbα antibody. Because a MoAb directed against GPIX is able to immunoprecipitate this abnormal band from detergent lysates of patient platelets, while AS-7, a MoAb directed against the amino-terminal portion of GPIbα, is not, the new band appears to represent an incomplete portion of GPIbα lacking the amino-terminal region of the peptide chain. Aberrant de novo synthesis of this region of the GPIbα chain appears unlikely, particularly in view of the absence of any DNA sequence abnormalities within the coding region of this gene, other than the single point mutation of a C to a T at nucleotide position 259. A more likely possibility would appear to be that this mutation, resulting in the substitution of a phenylalanine for the wild-type leucine at residue 57 of the mature GPIbα, alters the susceptibility of the chain to proteolytic degradation, resulting in GPIbα derivatives lacking the normal amino-terminal region.

In the present study, localization of the mutation to leucine-57 is particularly interesting, because this involves a highly conserved leucine residue within the leucine tandem repeat region of GPIbα (7,8,32). As Roth has recently reviewed (32), GPIbα is a member of a family of leucine-rich glycoproteins in which leucine residues appear at regular intervals within sequential 24 amino acid repeating segments ("tandem repeats"). The leucine tandem repeats must be distinguished from "leucine zippers" in which leucine residues occurring regularly at every seventh position are believed to promote association between polypeptide segments (33, 34), apparently through the formation of coiled coils (39, 40). While functional implications of the leucine tandem repeat motif are still largely speculative, the presence of hydrophobic and hydrophilic regions contributing to potentially amphipathic structures suggests that this motif may also be involved in associations between polypeptide segments (35, 36, 38, 41). If the leucine tandem repeats of GPIbα were indeed involved in such associations, then disruption of the tandem repeat by substitution of a phenylalanine for a highly conserved leucine might result in an abnormally increased exposure of the chain, with the possibility of increased susceptibility to proteolysis. If the substitution of phenylalanine at residue 57 produced a large enough perturbation of protein three-dimensional structure, increased sensitivity to proteolysis might even occur at sites distant from the mutation itself. Finally, the identification of bands at both 115 and 105 Kd by SDS-PAGE, after the reduction of all disulfide bonds, raises the possibility that proteolytic cleavage may be occurring at more than a single site.

We have consistently observed that the 140 Kd (non-reduced) immunoreactive GPIb found in these patients represents only a relatively small proportion of the total GPIb—never equal in amount to that comigrating with normal GPIb. If the hypothesis of increased susceptibility to proteolysis is correct, then this observation may be explained by the normally migrating GPIb from patient platelets representing protein coded for by both the normal and the mutant alleles, but where the abnormal GPIbα containing phenylalanine-57 has not yet undergone proteolytic degradation.

The major functional abnormalities of the patient platelets seen in vitro are a decreased binding affinity for native vWF demonstrable at low (0.5 mg/mL) ristocetin concentration, decreased vWF-dependent aggregation demonstrable at even relatively high (1.2 mg/mL) ristocetin concentration, and a decreased aggregation response to asialo-vWF. It is possible that the substitution of phenylalanine for leucine-57 produces a conformational change that does not favor the binding of vWF at relatively low ristocetin concentration and that impedes platelet agglutination or aggregation after the initial binding of vWF at higher ristocetin concentrations. The increased bleeding tendency of the affected patients may thus be related to impaired interaction between platelets and vWF in vivo. However, because all affected patients in this family are only heterozygous for the leucine to phenylalanine substitution, the presence of one normal allele may well allow the platelets to retain a degree of functional integrity sufficient to prevent the more severe bleeding tendency typically associated with classic BSD.

As discussed above, it is not currently known what role(s) the leucine tandem repeats may normally play within the GPIb/IX complex (32); indeed, the present study represents the first example of a perturbation of such a repeat within this complex. It is possible that GPIbα chains normally self-associate through the leucine tandem repeats, and that the phenylalanine-57 mutation reduces the extent of such self-association. A second possibility is that high affinity binding of vWF to the platelet GPIb/IX complex might be dependent on heterodimers forming between leucine tandem repeats of GPIbα and those present in GPIbβ (8), GPIX (9), or possibly even GPV (37). Alternatively, the leucine to phenylalanine mutation in GPIbα might produce changes in the three-dimensional structure of GPIbα directly affecting the binding sites for vWF. Additionally, because the natural occurrence of the phenylalanine-57 mutation has so far been observed only in heterozygous expression in patients showing autosomal dominant transmission of the disorder, in vitro production of this mutation may provide a means to observe the effects of an essentially homozygous expression upon vWF-platelet interactions.

EXPRESSION OF THE POLYPEPTIDES

The recombinant baculovirus expression vector system can be used for the production in insect cells of mutant polypeptides. Standard methods of site-directed mutagenesis were employed to create a codon coding for phenylalanine in place of the wild type leucine at codon 57 of the wild type human platelet GPIbα cDNA. The success of the site-directed mutagenesis was confirmed by DNA sequencing of the resultant mutant cDNA. Following this, the mutant full length cDNA was sub-cloned into the baculovirus transfer vector pVL 1392. This was accomplished by symmetric cloning into the Eco RI cloning site of the transfer vector. Following this, correct orientation of resulting constructs was determined by restriction mapping. A correctly oriented cDNA (i.e. correctly oriented with respect to the baculovirus promoter) was then grown up into a large plasmid preparation. Following this, using the standard methods in the manual of Summers and Smith (reference cited above), the plasmid containing the mutant full length GPIbα sequence can be co-transfected with wild-type baculovirus (*Autographa californica* nuclear polyhedrosis virus: AcNPV) into SF9 insect cells. A series of five rounds of dot-blot hybridizations can then be employed, in which multiple successive dilutions of the transfected cells are probed with a complementary DNA sequence representing genuine GPIbα. By this process of limiting dilutions, a purified recombinant virus that does not produce the polyhedra associated with the wild type baculovirus, but does show strong hybridization to the GPIbα probe, can be isolated. This virus is then used to infect fresh SF9 or subsequently SF21 insect cells. Recombinant protein corresponding to the mutant GPIbα protein is then harvested from the insect cells.

The expression of the wild-type GPIbα protein in insect cells resulted in a major protein band migrating at 78–80kD on SDS-PAGE. The band was electrophoretically transferred to nitrocellulose and stained in Western blots by polyclonal antibodies directed against both the carboxyl-terminal cytoplasmic end of platelet GPIbα (amino acids 582–600) and against the major extracellular portion of platelet GPIbα (glycocalicin). The recombinant wild-type protein distributed into the insoluble fraction of NP-40 extracts of insect cell lysates, but was solubilized in the presence of 6M guanidine. Subsequent removal of the guanidine by dialysis resulted in a semipurified source of soluble recombinant protein which inhibited von Willebrand factor (vWF) dependent platelet agglutination in a dose-dependent manner, with an $IC_{50}$ of approximately 1 μM. The recombinant protein was thus positively identified as GPIbα, wild type. An insect cell expresses DNA encoding sugars different from a mammalian cell, and proteins expressed in such insect cells characteristically migrate faster on SDS-PAGE than their naturally-occurring mammalian counterparts.

Similar procedures, such as SDS PAGE, can also be used to confirm the identity of a mutant polypeptide expressed by insect cells.

Although certain preferred embodiments have been depicted and described in detail herein, it will be apparent to those skilled in the relevant art that various modifications, additions, substitutions and the like can be made without departing from the spirit of the invention, and these are therefor considered to be within the scope of the invention as defined by the appended claims.

REFERENCES

1. Rosa, J. -P. et al., Blood 72:593 (1988).
2. Prandini, M. H. et al., Biochem Biophys Res Commun 156: 595 (1988).
3. Fitzgerald, L. A. et al., J Biol Chem 262: 3936 (1987).
4. Heidenreich, R. et al., Biochemistry 29: 1232 (1990).
5. Bray, P. F. et al., J Biol Chem 265: 9587 (1990).
6. Zimrin, A. B. et al., J Biol Chem 265: 8590 (1990).
7. Lopez, J. A. et al., Proc Natl Acad Sci USA 84: 5615 (1987).
8. Lopez, J. A. et al., Proc Natl Aca Sci USA 85: 2135 (1988). .
9. Hickey, M. J. et al., Proc Natl Acad Sci USA 86: 6773 (1989).
10. Hikey, M. J. et al., FEBS Lett 274: 189 (1990). Bray, P. F. and Shuman, M. A., Blood 75: 881 (1990).
12. Burk, C. D. et al., J Clin Invest 87: 270 (1991).
13. Ware, J. et al., Proc Natl Acad Sci USA 87: 2026 (1990).
14. Miller, J. L. et al., Proc Natl Acad Sci USA 88: 4761 (1991).
15. Miller, J. L. et al., Blood 70: 342a (1987).
16. DeMarco, L. et al., J Clin Invest 86: 25 (1990).
17. Aakhus, A. M. et al., Br J Haematol 74: 320 (1990).
18. Miller, J. L. et al., Blood 70: 1804 (1987).
19. Steiner, B. et al., Thromb Res 29: 43 (1983).
20. Miller, J. L. et al., Blood 68: 743 (1986).
21. Miller, J. L. et al., Br J Haematol 74: 313 (1990).
22. Kelton, J. G. et al., Am J Hematol 25: 299 (1987).
23. Laemmli, U. K., Nature 227: 680 (1970).
24. Towbin, H. et al., Proc Natl Acad Sci USA 76: 4350 (1979).
25. Walsh, P.N. et al., Br J Haematol 36: 281 (1977).
26. Fraker, P. J. and Speck, J. C. Jr., Biochem Biophys Res Commun 80: 849 (1978).
27. Mller, J. L. et al., J Clin Invest 72: 1532 (1983).
28. Munson, P. J. and Rodbard, D., Aal Biochem 107: 220 (1980).
29. Sambrook, J. et al., Molecular Cloning: A Laboratory Manual (Cold Spring Harbor Lab., Cold Spring Harbor, NY) (1989).
30. Wenger, R. H. et al., Biochem Biophys Res Commun 156: 389 (1988).
31. Petersen, E. et al., Blood 72: 335a (1988).
32. Roth, G. J., Blood 77: 5 (1991).
33. Landschulz, W. H. et al., Science 240: 1759 (1988).
34. Turner, R. and Tjian, R., Science 243: 1689 (1989).
35. Suzuki, N. et al., Proc Natl Acad Sci USA 87: 8711 (1990).
36. McFarland, K. C. et al., Science 245: 494 (1989).
37. Shimomura, T. et al., Blood 75: 2349 (1990).
38. Field, J. et al., Science 247: 464 (1990).
39. Rasmussen, R. et al, Proc Natl Acad Sci USA 88: 561 (1991).
40. O'Shea, E. K. et al., Science 243: 538 (1989).
41. Reinke, R. et al., Cell 52: 291 (1988).

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 610 amino acid residues
        ( B ) TYPE: amino acid
        ( D ) TOPOLOGY: linear ( i i ) MOLECULE TYPE: protein ( i x ) FEATURE:
        ( A ) NAME/KEY: GPIb sequence
        ( B ) LOCATION: 0 to 610

( x ) PUBLICATION INFORMATION:
        ( A ) AUTHORS: Lopez, Jose A., Chung, Dominic W.
                Fujikawa, Kazuo, Hagen, Frederick S.
                Papayannopoulou, Thalia
                Roth, Gerald J.
        ( B ) TITLE: Cloning of the chain of human platelet
                glycoprotein Ib: A transmembrane protein with
                homology to leucine-rich 2-glycoprotein
        ( C ) JOURNAL: Proc. Natl. Acad. Sci. USA
        ( D ) VOLUME: 84
        ( E ) ISSUE:
        ( F ) PAGES: 5615-5619
        ( G ) DATE: AUG-1987
        ( K ) RELEVANT RESIDUES IN SEQ ID NO: from 0 to 610

( x ) PUBLICATION INFORMATION:
        ( A ) AUTHORS: Zimmerman, Theodore S., Ruggeri, Zaverio M.
                Houghten, Richard A., Vincete, Vincete
                Mohri, Hiroshi,
        ( B ) TITLE: Proteolytic fragments and synthetic peptides that
                block the binding of von Willebrand factor to the
                platelet membrane glycoprotein Ib
        ( H ) DOCUMENT NUMBER: EP 0 317 278 A2
        ( I ) FILING DATE: 16-NOV-1988
        ( J ) PUBLICATION DATE: 24-MAY-1989
        ( K ) RELEVANT RESIDUES IN SEQ ID NO: from 0 to 293

( x i ) SEQUENCE DESCRIPTION: SEQ ID NO: 1:

```
            His   Pro   Ile   Cys   Glu   Val   Ser   Lys   Val   Ala   Ser   His   Leu   Glu   V
            5                             10                            15
            Cys   Asp   Lys   Arg   Asn   Leu   Thr   Ala   Leu   Pro   Pro   Asp   Leu   Pro   L
            20                            25                            30
            Thr   Thr   Ile   Leu   His   Leu   Ser   Glu   Asn   Leu   Leu   Tyr   Thr   Phe   S
            35                            40                            45
            Ala   Thr   Leu   Met   Pro   Tyr   Thr   Arg   Leu   Thr   Gln   Leu   Asn   Leu   A
            50                            55                            60
            Cys   Glu   Leu   Thr   Lys   Leu   Gln   Val   Asp   Gly   Thr   Leu   Pro   Val   L
            65                            70                            75
            Thr   Leu   Asp   Leu   Ser   His   Asn   Gln   Leu   Gln   Ser   Leu   Pro   Leu   L
            80                            85                            90
            Gln   Thr   Leu   Pro   Ala   Leu   Thr   Val   Leu   Asp   Val   Ser   Phe   Asn   A
            100                           105                           110
            Thr   Ser   Leu   Pro   Leu   Gly   Ala   Leu   Arg   Gly   Leu   Gly   Glu   Leu   G
            115                           120                           125
            Leu   Tyr   Leu   Lys   Val   Asn   Glu   Leu   Lys   Thr   Leu   Pro   Pro   Gly   L
            130                           135                           140
            Thr   Pro   Thr   Pro   Lys   Leu   Glu   Lys   Leu   Ser   Leu   Ala   Asn   Asn   A
            145                           150                           155
            Thr   Glu   Leu   Pro   Val   Gly   Leu   Leu   Asn   Gly   Leu   Glu   Asn   Leu   A
            160                           165                           170
            Leu   Leu   Leu   Gln   Glu   Asn   Ser   Leu   Tyr   Thr   Ile   Pro   Lys   Gly   P
            180                           185                           190
            Gly   Ser   His   Leu   Leu   Pro   Phe   Ala   Phe   Leu   His   Gly   Asn   Pro   T
            195                           200                           205
            Cys   Asn   Cys   Glu   Ile   Leu   Tyr   Phe   Arg   Arg   Trp   Leu   Gln   Asp   A
            210                           215                           220
            Glu   Asn   Val   Tyr   Val   Trp   Lys   Gln   Gly   Val   Asp   Val   Lys   Ala   M
            225                           230                           235
            Ser   Asn   Val   Ala   Ser   Val   Gln   Cys   Asp   Asn   Ser   Asp   Lys   Phe   P
            245                           250                           255
            Tyr   Lys   Tyr   Pro   Gly   Lys   Gly   Cys   Pro   Thr   Leu   Gly   Asp   Glu   G
            260                           265                           270
            Thr   Asp   Leu   Tyr   Asp   Tyr   Pro   Glu   Glu   Asp   Thr   Glu   Gly   A
            275                           280                           285
            Val   Arg   Ala   Thr   Arg   Thr   Val   Val   Lys   Phe   Pro   Thr   Lys   Ala   H
            290                           295                           300
            Thr   Pro   Trp   Gly   Leu   Phe   Tyr   Ser   Trp   Ser   Thr   Ala   Ser   Leu   A
            305                           310                           315
```

-continued

| | | | | | | | | | | | | |
|---|---|---|---|---|---|---|---|---|---|---|---|---|
| Gln 325 | Met | Pro | Ser | Ser | Leu 330 | His | Pro | Thr | Gln | Glu 335 | Ser | Thr | Lys | G |
| Thr 340 | Thr | Phe | Pro | Pro | Arg 345 | Trp | Thr | Pro | Asn | Phe 350 | Thr | Leu | His | M |
| Ser 355 | Ile | Thr | Phe | Ser | Lys 360 | Thr | Pro | Lys | Ser | Thr 365 | Thr | Glu | Pro | T |
| Ser 370 | Pro | Thr | Thr | Ser | Glu 375 | Pro | Val | Pro | Glu | Pro 380 | Ala | Pro | Asn | M |
| Thr 385 | Leu | Glu | Pro | Thr | Pro 390 | Ser | Pro | Thr | Thr | Pro 395 | Glu | Pro | Thr | S |
| Pro 405 | Ala | Pro | Ser | Pro | Thr 410 | Thr | Pro | Glu | Pro | Thr 415 | Pro | Ile | Pro | T |
| Ala 420 | Thr | Ser | Pro | Thr | Ile 425 | Leu | Val | Ser | Ala | Thr 430 | Ser | Leu | Ile | T |
| Lys 435 | Ser | Thr | Phe | Leu | Thr 440 | Thr | Thr | Lys | Pro | Val 445 | Ser | Leu | Leu | G |
| Thr 450 | Lys | Lys | Thr | Ile | Pro 455 | Glu | Leu | Asp | Gln | Pro 460 | Pro | Lys | Leu | A |
| Val 465 | Leu | Gln | Gly | His | Leu 470 | Glu | Ser | Ser | Arg | Asn 475 | Asp | Pro | Phe | L |
| Pro 485 | Asp | Phe | Cys | Cys | Leu 490 | Leu | Pro | Leu | Gly | Phe 495 | Tyr | Val | Leu | G |
| Phe 500 | Trp | Leu | Leu | Phe | Ala 505 | Ser | Val | Val | Leu | Ile 510 | Leu | Leu | Leu | S |
| Val 515 | Gly | His | Val | Lys | Pro 520 | Gln | Ala | Leu | Asp | Ser 525 | Gly | Gln | Gly | A |
| Leu 530 | Thr | Thr | Ala | Thr | Gln 535 | Thr | Thr | His | Leu | Glu 540 | Leu | Gln | Arg | G |
| Gln 545 | Val | Thr | Val | Pro | Arg 550 | Ala | Trp | Leu | Leu | Phe 555 | Leu | Arg | Gly | S |
| Pro 565 | Thr | Phe | Arg | Ser | Ser 570 | Leu | Phe | Leu | Trp | Val 575 | Arg | Pro | Asn | G |
| Val 580 | Gly | Pro | Leu | Val | Ala 585 | Gly | Arg | Arg | Pro | Ser 590 | Ala | Leu | Ser | G |
| Arg 595 | Gly | Gln | Asp | Leu | Leu 600 | Ser | Thr | Val | Ser | Ile 605 | Arg | Tyr | Ser | G |
| Ser 610 | Leu | | | | | | | | | | | | | |

What is claimed is:

1. A purified polypeptide encoded by a DNA sequence, said DNA sequence comprising DNA encoding naturally-occurring wild-type platelet glycoprotein Ib alpha having a mutation which renders said polypeptide encoded by said DNA less reactive with Von Willebrand factor, said mutation comprising an amino acid substitution for a leucine residue at amino acid 57.

2. The purified polypeptide of claim 1 wherein said amino acid substituted for leucine comprises phenylalanine.

3. A composition comprising an amount of the polypeptide of claim 1 effective to inhibit platelet aggregation and a compatible carrier.

4. A pharmaceutical composition comprising an amount of the polypeptide of claim 1 effective to inhibit platelet aggregation and a pharmaceutically acceptable carrier.

5. A method of inhibiting platelet aggregation which comprises contacting the platelets with an amount of the polypeptide of claim 1 effective to inhibit aggregation of the platelets.

6. A method of reducing the aggregation of platelets which comprises introducing a mutant platelet glycoprotein Ib alpha into said platelets, said mutant comprising platelet glycoprotein Ib alpha having an amino acid substitution for a leucine at amino acid 57, thereby rendering said platelets less reactive with von Willebrand factor, and thereby reducing aggregation of said platelets.

7. A polypeptide of claim 1 bound to a thrombolytic agent.

8. The polypeptide bound to a thrombolytic agent of claim 7, wherein the thrombolytic agent is selected from the group consisting of: tissue plasminogen activator (TPA), urokinase, Streptokinase, prourokinase, Anisoylated Plasminogen-Streptokinase Activator Complex, TPA analogs, or a protease.

* * * * *

UNITED STATES PATENT AND TRADEMARK OFFICE
CERTIFICATE OF CORRECTION

PATENT NO.   : 5,298,239
DATED        : March 29, 1994
INVENTOR(S)  : Miller et al.

It is certified that error appears in the above-indentified patent and that said Letters Patent is hereby corrected as shown below:

In columns 3-8, after line 47, delete the amino acid sequence for SEQ ID NO: 6 and replace it with the following partially renumbered amino acid sequence:

In columns 21-24, replace the Sequence Listing with the following Sequence Listing: (As per attached sheets).

Signed and Sealed this

Third Day of October, 1995

*Attest:*

BRUCE LEHMAN

*Attesting Officer*          Commissioner of Patents and Trademarks

```
His Pro Ile Cys Glu Val Ser Lys Val Ala Ser His Leu Glu Val Asn
1             5                 10                      15
Cys Asp Lys Arg Asn Leu Thr Ala Leu Pro Pro Asp Leu Pro Lys Asp
             20                 25                 30
Thr Thr Ile Leu His Leu Ser Glu Asn Leu Leu Tyr Thr Phe Ser Leu
             35                 40                 45
Ala Thr Leu Met Pro Tyr Thr Arg Leu Thr Gln Leu Asn Leu Asp Arg
     50                 55                 60
Cys Glu Leu Thr Lys Leu Gln Val Asp Gly Thr Leu Pro Val Leu Gly
65                 70                 75                      80
Thr Leu Asp Leu Ser His Asn Gln Leu Gln Ser Leu Pro Leu Leu Gly
             85                 90                 95
Gln Thr Leu Pro Ala Leu Thr Val Leu Asp Val Ser Phe Asn Arg Leu
             100                105                110
```

```
Thr Ser Leu Pro Leu Gly Ala Leu Arg Gly Leu Gly Glu Leu Gln Glu
        115             120             125
Leu Tyr Leu Lys Val Asn Glu Leu Lys Thr Leu Pro Pro Gly Leu Leu
        130             135             140
Thr Pro Thr Pro Lys Leu Glu Lys Leu Ser Leu Ala Asn Asn Asn Leu
145             150             155             160
Thr Glu Leu Pro Val Gly Leu Leu Asn Gly Leu Glu Asn Leu Asp Thr
                165             170             175
Leu Leu Leu Gln Glu Asn Ser Leu Tyr Thr Ile Pro Lys Gly Phe Phe
        180             185             190
Gly Ser His Leu Leu Pro Phe Ala Phe Leu His Gly Asn Pro Trp Leu
        195             200             205
Cys Asn Cys Glu Ile Leu Tyr Phe Arg Arg Trp Leu Gln Asp Asn Ala
        210             215             220
Glu Asn Val Tyr Val Trp Lys Gln Gly Val Asp Val Lys Ala Met Thr
225             230             235             240
Ser Asn Val Ala Ser Val Gln Cys Asp Asn Ser Asp Lys Phe Pro Val
                245             250             255
Tyr Lys Tyr Pro Gly Lys Gly Cys Pro Thr Leu Gly Asp Glu Gly Asp
                260             265             270
Thr Asp Leu Tyr Asp Tyr Tyr Pro Glu Glu Asp Thr Glu Gly Asp Lys
        275             280             285
Val Arg Ala Thr Arg Thr Val Val Lys Phe Pro Thr Lys Ala His Thr
        290             295             300
Thr Pro Trp Gly Leu Phe Tyr Ser Trp Ser Thr Ala Ser Leu Asp Ser
305             310             315             320
Gln Met Pro Ser Ser Leu His Pro Thr Gln Glu Ser Thr Lys Glu Gln
                325             330             335
Thr Thr Phe Pro Pro Arg Trp Thr Pro Asn Phe Thr Leu His Met Glu
                340             345             350
```

```
Ser Ile Thr Phe Ser Lys Thr Pro Lys Ser Thr Thr Glu Pro Thr Pro
    355             360             365
Ser Pro Thr Thr Ser Glu Pro Val Pro Glu Pro Ala Pro Asn Met Thr
    370             375             380
Thr Leu Glu Pro Thr Pro Ser Pro Thr Thr Pro Glu Pro Thr Ser Glu
385             390             395                             400
Pro Ala Pro Ser Pro Thr Thr Pro Glu Pro Thr Pro Ile Pro Thr Ile
            405             410             415
Ala Thr Ser Pro Thr Ile Leu Val Ser Ala Thr Ser Leu Ile Thr Pro
            420             425             430
Lys Ser Thr Phe Leu Thr Thr Thr Lys Pro Val Ser Leu Leu Glu Ser
        435             440             445
Thr Lys Lys Thr Ile Pro Glu Leu Asp Gln Pro Pro Lys Leu Arg Gly
    450             455             460
Val Leu Gln Gly His Leu Glu Ser Ser Arg Asn Asp Pro Phe Leu His
465             470             475                             480
Pro Asp Phe Cys Cys Leu Leu Pro Leu Gly Phe Tyr Val Leu Gly Leu
            485             490             495
Phe Trp Leu Leu Phe Ala Ser Val Val Leu Ile Leu Leu Leu Ser Trp
        500             505             510
Val Gly His Val Lys Pro Gln Ala Leu Asp Ser Gly Gln Gly Ala Ala
        515             520             525
Leu Thr Thr Ala Thr Gln Thr Thr His Leu Glu Leu Gln Arg Gly Arg
    530             535             540
Gln Val Thr Val Pro Arg Ala Trp Leu Leu Phe Leu Arg Gly Ser Leu
545             550             555                             560
Pro Thr Phe Arg Ser Ser Leu Phe Leu Trp Val Arg Pro Asn Gly Arg
            565             570             575
```

```
        Val Gly Pro Leu Val Ala Gly Arg Arg Pro Ser Ala Leu Ser Gln Gly
                580                 585                 590

Arg Gly Gln Asp Leu Leu Ser Thr Val Ser Ile Arg Tyr Ser Gly His
                595                 600                 605

Ser Leu
        610
```

In columns 21-24, replace the SEQUENCE LISTING with the following SEQUENCE LISTING:

SEQUENCE LISTING (1) GENERAL INFORMATION:

(i) APPLICANT: Miller, Jonathan L.
                    Cunningham, David
                      Lyle, Vicki A.
                      Finch, Clara N.

(ii) TITLE OF INVENTION: MUTATIONS RENDERING PLATELET GLYCOPROTEIN Ib ALPHA LESS REACTIVE (iii) NUMBER OF SEQUENCES: 6

(iv) CORRESPONDENCE ADDRESS:
        (A) ADDRESSEE: Nixon, Hargrave, Devans & Doyle
        (B) STREET: Clinton Square, P.O. Box 1051
        (C) CITY: Rochester
        (D) STATE: New York
        (E) COUNTRY: USA
        (F) ZIP: 14603

(v) COMPUTER READABLE FORM:
    (A) MEDIUM TYPE: Floppy disk
    (B) COMPUTER: IBM PC compatible
    (C) OPERATING SYSTEM: PC-DOS/MS-DOS
    (D) SOFTWARE: PatentIn Release #1.0, Version #1.30

(vi) CURRENT APPLICATION DATA:
    (A) APPLICATION NUMBER: US 08/119,262
    (B) FILING DATE: 09-SEP-1993
    (C) CLASSIFICATION:

(vii) PRIOR APPLICATION DATA:
    (A) APPLICATION NUMBER: US 07/821,717
    (B) FILING DATE: 15-JAN-1992

(viii) ATTORNEY/AGENT INFORMATION:
    (A) NAME: Timain, Susan J.
    (B) REGISTRATION NUMBER: 34,103
    (C) REFERENCE/DOCKET NUMBER: 20884/22

(ix) TELECOMMUNICATION INFORMATION:
    (A) TELEPHONE: (716) 263-1636
    (B) TELEFAX: (716) 263-1600

(2) INFORMATION FOR SEQ ID NO:1:

(i) SEQUENCE CHARACTERISTICS:
    (A) LENGTH: 31 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

TACTGAATTC CTCATGCCTC TCCTCCTCTT G          31

(2) INFORMATION FOR SEQ ID NO:2:

(i) SEQUENCE CHARACTERISTICS:
      (A) LENGTH: 31 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:2:

TTGTCCTGCA GCCAGCGACG AAAATAGAGG A          31

(2) INFORMATION FOR SEQ ID NO:3:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:3:

CCGGATCCCA ACTAGATTCC AATAGGAGAG                    30

(2) INFORMATION FOR SEQ ID NO:4:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:4:

CTGAGTGAGG CGAGTG                                16

(2) INFORMATION FOR SEQ ID NO:5:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:5:

CTGAGTGAAG CGAGTG                16

(2) INFORMATION FOR SEQ ID NO:6:

(i) SEQUENCE CHARACTERISTICS:
        (A) LENGTH: 610 amino acids
        (B) TYPE: amino acid
        (C) STRANDEDNESS:
        (D) TOPOLOGY: linear (ii) MOLECULE TYPE: protein (x) PUBLICATION INFORMATION:
        (A) AUTHORS: Lopez, Jose A.
                  Chung, Dominic W.
                  Fujikawa, Kazuo
                  Hagen, Frederick S.
                  Papayannopoulou, Thalia
                  Roth, Gerald J.

(B) TITLE: Cloning of the alpha chain of
human platelet glycoprotein Ib: A transmembrane protein
with homology to leucine-rich alpha-2-glycoprotein
            (C) JOURNAL: Proc. Natl. Acad. Sci. U.S.A.
            (D) VOLUME: 84
            (F) PAGES: 5615-5619
            (G) DATE: AUG-1987
            (K) RELEVANT RESIDUES IN SEQ ID NO:6: FROM 0
                TO 610

(x) PUBLICATION INFORMATION:
            (A) AUTHORS: Zimmerman, Theodore S.
                         Ruggeri, Zaverio M.
                         Houghten, Richard A.
                         Vincete, Vincete
                         Mohri, Hiroshi
            (B) TITLE: Proteolytic fragments and
synthetic peptides that block the binding of von
Willebrand factor to the platelet membrane glycoprotein
Ib
            (H) DOCUMENT NUMBER: EP 0 317 278 A2
            (I) FILING DATE: 16-NOV-1988
            (J) PUBLICATION DATE: 24-MAY-1989
            (K) RELEVANT RESIDUES IN SEQ ID NO:6: FROM 0
                TO 293

(xi) SEQUENCE DESCRIPTION: SEQ ID NO:6:

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
            20                  25                  30

Thr Thr Ile Leu His Leu Ser Glu Asn Leu Leu Tyr Thr Phe Ser Leu
        35                  40                  45

```
Ala Thr Leu Met Pro Tyr Thr Arg Leu Thr Gln Leu Asn Leu Asp Arg
    50                  55                  60
Cys Glu Leu Thr Lys Leu Gln Val Asp Gly Thr Leu Pro Val Leu Gly
65                  70                  75                  80
Thr Leu Asp Leu Ser His Asn Gln Leu Gln Ser Leu Pro Leu Leu Gly
                85                  90                  95
Gln Thr Leu Pro Ala Leu Thr Val Leu Asp Val Ser Phe Asn Arg Leu
            100                 105                 110
Thr Ser Leu Pro Leu Gly Ala Leu Arg Gly Leu Gly Glu Leu Gln Glu
        115                 120                 125
Leu Tyr Leu Lys Val Asn Glu Leu Lys Thr Leu Pro Pro Gly Leu Leu
    130                 135                 140
Thr Pro Thr Pro Lys Leu Glu Lys Leu Ser Leu Ala Asn Asn Asn Leu
145                 150                 155                 160
Thr Glu Leu Pro Val Gly Leu Leu Asn Gly Leu Glu Asn Leu Asp Thr
                165                 170                 175
Leu Leu Leu Gln Glu Asn Ser Leu Tyr Thr Ile Pro Lys Gly Phe Phe
            180                 185                 190
Gly Ser His Leu Leu Pro Phe Ala Phe Leu His Gly Asn Pro Trp Leu
        195                 200                 205
Cys Asn Cys Glu Ile Leu Tyr Phe Arg Arg Trp Leu Gln Asp Asn Ala
    210                 215                 220
Glu Asn Val Tyr Val Trp Lys Gln Gly Val Asp Val Lys Ala Met Thr
225                 230                 235                 240
Ser Asn Val Ala Ser Val Gln Cys Asp Asn Ser Asp Lys Phe Pro Val
                245                 250                 255
Tyr Lys Tyr Pro Gly Lys Gly Cys Pro Thr Leu Gly Asp Glu Gly Asp
            260                 265                 270
```

```
Thr Asp Leu Tyr Asp Tyr Tyr Pro Glu Glu Asp Thr Glu Gly Asp Lys
        275             280                 285
Val Arg Ala Thr Arg Thr Val Val Lys Phe Pro Thr Lys Ala His Thr
    290             295                 300
Thr Pro Trp Gly Leu Phe Tyr Ser Trp Ser Thr Ala Ser Leu Asp Ser
305             310                 315                     320
Gln Met Pro Ser Ser Leu His Pro Thr Gln Glu Ser Thr Lys Glu Gln
            325                 330                 335
Thr Thr Phe Pro Pro Arg Trp Thr Pro Asn Phe Thr Leu His Met Glu
            340                 345                 350
Ser Ile Thr Phe Ser Lys Thr Pro Lys Ser Thr Thr Glu Pro Thr Pro
        355                 360                 365
Ser Pro Thr Thr Ser Glu Pro Val Pro Glu Pro Ala Pro Asn Met Thr
    370                 375                 380
Thr Leu Glu Pro Thr Pro Ser Pro Thr Thr Pro Glu Pro Thr Ser Glu
385             390                 395                     400
Pro Ala Pro Ser Pro Thr Thr Pro Glu Pro Thr Pro Ile Pro Thr Ile
            405                 410                 415
Ala Thr Ser Pro Thr Ile Leu Val Ser Ala Thr Ser Leu Ile Thr Pro
            420                 425                 430
Lys Ser Thr Phe Leu Thr Thr Thr Lys Pro Val Ser Leu Leu Glu Ser
            435                 440                 445
Thr Lys Lys Thr Ile Pro Glu Leu Asp Gln Pro Pro Lys Leu Arg Gly
    450                 455                 460
Val Leu Gln Gly His Leu Glu Ser Ser Arg Asn Asp Pro Phe Leu His
465             470                 475                     480
Pro Asp Phe Cys Cys Leu Leu Pro Leu Gly Phe Tyr Val Leu Gly Leu
            485                 490                 495
Phe Trp Leu Leu Phe Ala Ser Val Val Leu Ile Leu Leu Leu Ser Trp
            500                 505                 510
```

```
Val Gly His Val Lys Pro Gln Ala Leu Asp Ser Gly Gln Gly Ala Ala
    515                 520                 525
Leu Thr Thr Ala Thr Gln Thr Thr His Leu Glu Leu Gln Arg Gly Arg
    530                 535                 540
Gln Val Thr Val Pro Arg Ala Trp Leu Leu Phe Leu Arg Gly Ser Leu
545                 550                 555                 560
Pro Thr Phe Arg Ser Ser Leu Phe Leu Trp Val Arg Pro Asn Gly Arg
                565                 570                 575
Val Gly Pro Leu Val Ala Gly Arg Arg Pro Ser Ala Leu Ser Gln Gly
            580                 585                 590
Arg Gly Gln Asp Leu Leu Ser Thr Val Ser Ile Arg Tyr Ser Gly His
    595                 600                 605
Ser Leu
    610
```